(12) United States Patent
Kaminski et al.

(10) Patent No.: US 7,892,838 B2
(45) Date of Patent: Feb. 22, 2011

(54) METHOD FOR THE IN VIVO MODIFICATION OF THE SYNTHESIS ACTIVITY OF A METABOLITE BY MEANS OF THE MODIFICATION OF A GENE THE ACTIVITY OF WHICH IS NOT THE ORIGINAL ACTIVITY

(75) Inventors: Pierre-Alexandre Kaminski, Paris (FR); Philippe Marliere, Paris (FR)

(73) Assignees: Institut Pasteur, Paris (FR); Centre National de la Recherche Scientifique (CNRS), Paris (FR)

( * ) Notice: Subject to any disclaimer, the term of this patent is extended or adjusted under 35 U.S.C. 154(b) by 284 days.

(21) Appl. No.: 11/735,148

(22) Filed: Apr. 13, 2007

(65) Prior Publication Data

US 2008/0299608 A1  Dec. 4, 2008

Related U.S. Application Data

(63) Continuation of application No. 10/550,618, filed as application No. PCT/FR2004/000744 on Mar. 25, 2004, now abandoned.

(30) Foreign Application Priority Data

Mar. 28, 2003  (FR) .................................. 03 03910

(51) Int. Cl.
| | |
|---|---|
| C12P 21/06 | (2006.01) |
| C12P 19/30 | (2006.01) |
| C12N 9/10 | (2006.01) |
| C12N 1/20 | (2006.01) |
| C12N 15/00 | (2006.01) |
| C12N 15/74 | (2006.01) |
| C07H 21/02 | (2006.01) |
| C07H 21/04 | (2006.01) |

(52) U.S. Cl. .................. 435/471; 435/69.1; 435/89; 435/193; 435/252.33; 435/320.1; 435/455; 536/23.1; 536/23.2

(58) Field of Classification Search ................ None
See application file for complete search history.

(56) References Cited

U.S. PATENT DOCUMENTS 7,381,555 B2 *  6/2008  Kaminski et al. ........... 435/193
7,547,513 B2 *  6/2009  Marliere et al. ................ 435/6

FOREIGN PATENT DOCUMENTS

WO  02/083892  10/2002

WO  03/025163  3/2003

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Wang Xing-Guo et al, "Conversion of a glutamate dehydrogenase into methionine/norleucine dehydrogenase by site-directed mutagenesis", European journal of Biochemistry, vol. 268, No. 22, pp. 5791-5799, 2001.
Wan Lianglu et al, "In vitro evolution of horse heart myoglobin to increase peroxidase activity", proceedings of the National Academy of Sciences of the United States of America, vol. 95, No. 22, pp. 12825-12831, 1998.
Chen K. et al., "Enzyme engineering for nonaqueous solvents: Random mutagenesis to enhance activity of subtilisin E in Polar organic media", Elsevier Science Publishers, vol. 9, No. 11, pp. 1073-1077, 1991.
Carson Dennis A. et al, "Synthesis of 2, 3—Dideoxynucleosides by Enzymatic Transglycosylation" , Biochemical and Biophysical Research Communications, vol. 155, No. 2, pp. 829-834, 1988.
Huang Min-Chi et al, "Analogs of 2'-Deoxyadenosine: Facile Enzymatic Preparation and Growth Inhibitory Effects on Human Cell Lines", Biochemical Pharmacology, vol. 30, No. 19, pp. 2663-2671, 1981.
Freeman G.A. et al, "2-amino-9-(3-azido-2,3-dideoxy-beta-D-erythro-pentofuranosyl)-6-substituted-9H-purines:Synthesis and anti-HIV activity.", Bioorganic & Medicinal Chemistry, vol. 3, No. 4, pp. 447-458, 1995.
Short Steven A. et al., "Active site amino acids that participate in the catalytic mechanism of nucleoside 2'-deoxyribosyltransferase"< Journal of Biological Chemistry, vol. 271, No. 9, pp. 4978-4987, 1996.

* cited by examiner

*Primary Examiner*—Christian L Fronda
(74) *Attorney, Agent, or Firm*—Oblon, Spivak, McClelland, Maier & Neustadt, L.L.P.

(57) ABSTRACT

The invention relates to a method for altering a protein X such as to modify the characteristics thereof by a) obtaining the mutants X* of the sequence coding for protein X, by means of aleatory mutagenesis, b) transformation of cells with a phenotype [P-] with vectors comprising the mutated nucleic acids obtained in step (a) which code for proteins X*, where P-signifies that said cells are auxotrophic for substance P, P begin the product of the action of X on the natural substrate thereof S, c) culturing said cells in a medium comprising a substrate S*, S* being an analogue of the natural substrate S of the protein X, d) selection of the cells [P-:: X*] which have survived step c) in which the proteins X* can biosynthesise the product P from the substrate S*. The invention further relates to mutated proteins X, nucleic acids, expression vectors, host cells comprising a vector, use of N-dideoxyribosyl transferases for the transfer of a dideoxyribose (ddR) from a dideoxyribonucleoside to another nucleoside, a method for production of compounds comprising a step using a mutated protein and a strain of *E. coli*.

11 Claims, 7 Drawing Sheets

Figure 1:
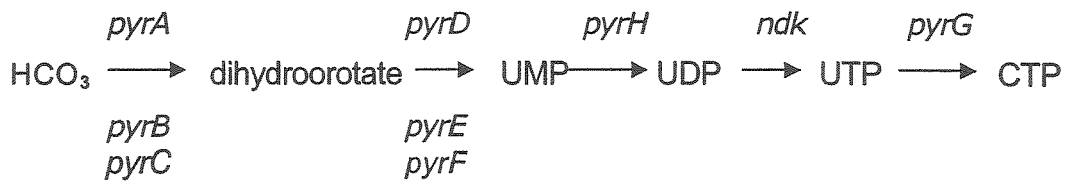

Figure la: Diagram of the "de novo" pathway of UTP and CTP in E. coli ndk: nucleoside diphosphokinase pyrA: carbamoylphosphate synthase pyrB: aspartate carbamoyltransferase pyrC: dihydroorotase pyrD: dihydroorotate oxydase pyrE: orotate phosphoribosyltransferase pyrF: orotidine 5'-phosphate decarboxylase pyrG: CTP synthetase pyrH: UMP kinase

Figure lb: Recycling route of pyrimidines in *E. coli*

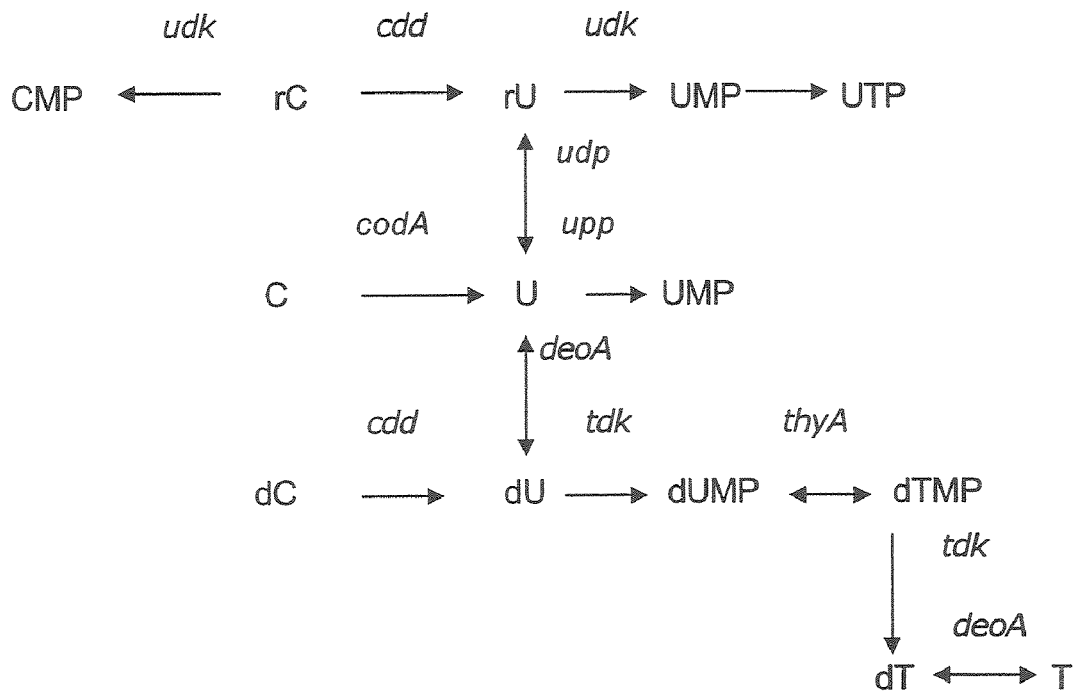

*cdd:* cytidine/deoxycitidine deaminase
*cmk.* CMP/dCMP kinase horylase
*codA:* cytosine deaminase
*deoA:* thymidine phosphorylase
*tdk:* thymidine kinase
*udk:* uridine/cytidine kinase
*udp:* uridine phosphorylase
*upp:* uridine phosphoryltransferase
*thyA:* thymidylate synthase The enzymes are represented above by their corresponding genes.

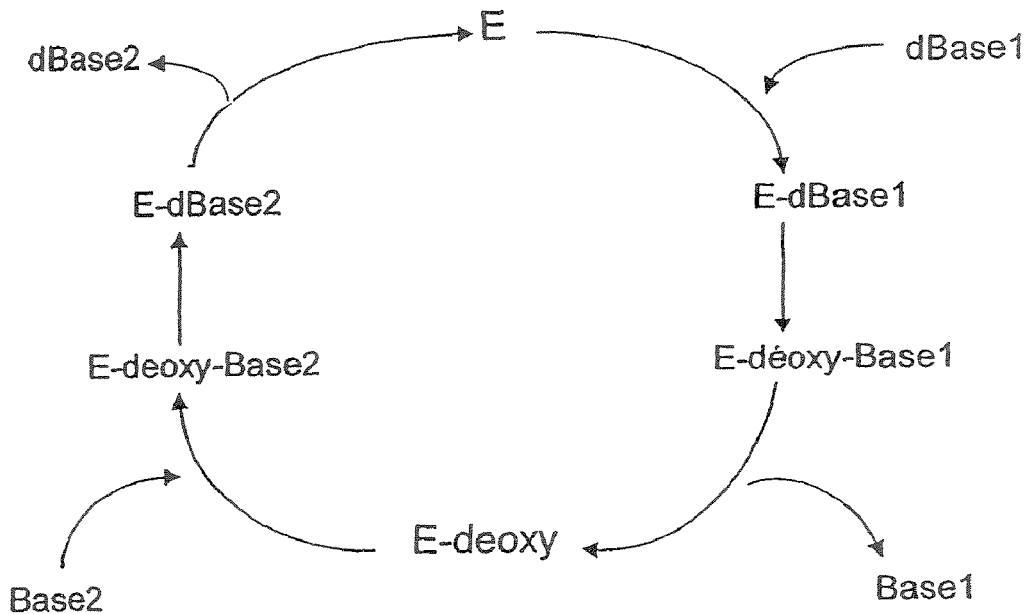
* E-deoxy = enzyme-deoxyribose of the form
  (E = active site of the enzyme)
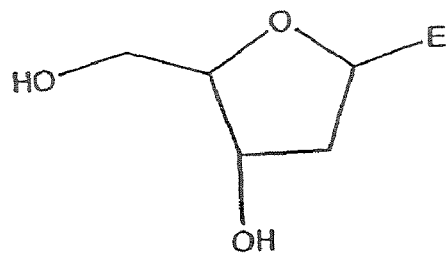
*dbase = deoxyribonucleotide
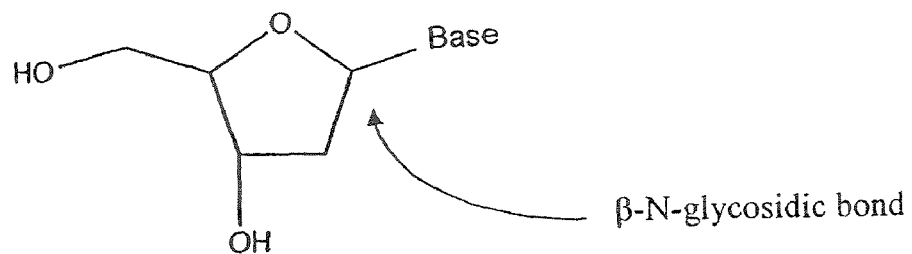
β-N-glycosidic bond
Figure 2

SEQUENCE LISTING

<160> NUMBER OF SEQ ID NOS: 15

<210> SEQ ID NO 1
<211> LENGTH: 474

```
<212> TYPE: DNA
<213> ORGANISM: Lactobacillus leichmannii
<220> FEATURE:
<221> NAME/KEY: MISC_FEATURE
<222> LOCATION: (1)..(474)
<223> OTHER INFORMATION: Coding region of the N-deoxyribosyltransferase
      gene (dtp)

<400> SEQUENCE: 1
atgccaaaaa agacgatcta cttcggtgcc ggctggttca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg tgtctacat ccctgacgaa gaagacgtcg gcctgggcat ggaactgggt      300
tacgccttga gccaaggcaa gtacgtcctt ttggtcatcc ggacgaaga ctacggcaag      360 ccgatcaacc tcatgagctg ggcgtcagc gacaacgtga tcaagatgag ccagctgaag      420
gacttcaact tcaacaagcc gcgcttcgac ttctacgaag gtgccgtata ctaa            474

<210> SEQ ID NO 2
<211> LENGTH: 157
<212> TYPE: PRT
<213> ORGANISM: Lactobacillus leichmannii
<220> FEATURE:
<221> NAME/KEY: MISC_FEATURE
<222> LOCATION: (1)..(157)
<223> OTHER INFORMATION: N-deoxyribosyltransferase carrying the mutation
      G9S
<220> FEATURE:
<221> NAME/KEY: MISC_FEATURE
<222> LOCATION: (9)..(9)
<223> OTHER INFORMATION: serine/glycine mutation

<400> SEQUENCE: 2

Met Pro Lys Lys Thr Ile Tyr Phe Ser Ala Gly Trp Phe Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Glu Asp Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Asn Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 3
<211> LENGTH: 474
<212> TYPE: DNA
<213> ORGANISM: Lactobacillus leichmannii
<220> FEATURE:
```

```
<221> NAME/KEY: MISC_FEATURE
<222> LOCATION: (1)..(474)
<223> OTHER INFORMATION: Coding sequence of mutated
      N-deoxyribosyltransferase (NTD*)

<400> SEQUENCE: 3
atgccaaaaa agacgatcta cttcagtgcc ggctggttca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gcgtctacat ccctgacgaa gaagacgtcg gcctgggcat ggaactgggt     300
tacgccttga gccaaggcaa gtacgtcctt ttggtcatcc ggacgaaga ctacggcaag      360 ccgatcaacc tcatgagctg gggcgtcagc gacaacgtga tcaagatgag ccagctgaag     420
gacttcaact tcaacaagcc gcgcttcgac ttctacgaag gtgccgtata ctaa           474

<210> SEQ ID NO 4
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n is a, t, g or c
<220> FEATURE:
<221> NAME/KEY: MISC_FEATURE
<222> LOCATION: (2)..(2)
<223> OTHER INFORMATION: n is a, t, g or c
<220> FEATURE:
<221> NAME/KEY: MISC_FEATURE
<222> LOCATION: (3)..(3)
<223> OTHER INFORMATION: n is a, t, g or c

<400> SEQUENCE: 4
nnncccgggc ttcttgctcg cttctcgttt gg                                    32

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n is a, t, g or c
<220> FEATURE:
<221> NAME/KEY: MISC_FEATURE
<222> LOCATION: (2)..(2)
<223> OTHER INFORMATION: n is a, t, g or c

<400> SEQUENCE: 5
nnggatccgt ttgaccgtag cgggcgaac                                        29

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n is a, t, g, or c
```

<400> SEQUENCE: 6
ngaattctta ttcgacactg ttagcctcc                                   29

<210> SEQ ID NO 7
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n is a, t, g or c

<400> SEQUENCE: 7
ngaattcacg actgggttac agcgagc                                     27

<210> SEQ ID NO 8
<211> LENGTH: 35
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n is a, t, g or c
<220> FEATURE:
<221> NAME/KEY: MISC_FEATURE
<222> LOCATION: (2)..(2)
<223> OTHER INFORMATION: n is a, t, g or c
<220> FEATURE:
<221> NAME/KEY: MISC_FEATURE
<222> LOCATION: (3)..(3)
<223> OTHER INFORMATION: n is a, t, g or c

<400> SEQUENCE: 8
nnncccgggg ccgacctgct ggcccactct gacgg                            35

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n = a, t, g or c
<220> FEATURE:
<221> NAME/KEY: MISC_FEATURE
<222> LOCATION: (2)..(2)
<223> OTHER INFORMATION: n = a, t, g or c

<400> SEQUENCE: 9
nnggatcccc cggcggcagc gcctacggaa ccgctgcc                         38

<210> SEQ ID NO 10
<211> LENGTH: 37
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n = a, t, g or c

<400> SEQUENCE: 10
ngaattctta atcagtaaat ggaatgacaa tttcgcc                          37

<210> SEQ ID NO 11
<211> LENGTH: 34
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n = a, t, g or c

<400> SEQUENCE: 11
ngaattcaaa tcgtagcttc ctgttgtcat tagg                       34

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
cgccagggtt ttcccagtca cg                                    22

<210> SEQ ID NO 13
<211> LENGTH: 23
<212> TYPE: DNA
<213> ORGANISM: Artificial Sequence
<220> FEATURE:
<223> OTHER INFORMATION: Synthetic DNA

<400> SEQUENCE: 13
agcggataac aatttcacac agg                                   23

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
gatatacata tgccaaaaaa gacgatctac                            30

<210> SEQ ID NO 15
<211> LENGTH: 36
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (1)..(1)
<223> OTHER INFORMATION: n = a, t, g or c
<220> FEATURE:
<221> NAME/KEY: MISC_FEATURE
<222> LOCATION: (2)..(2)
<223> OTHER INFORMATION: n = a, t, g or c

<400> SEQUENCE: 15
nnggatcctt agtatacggc accttcgtag aagtcg                     36

METHOD FOR THE IN VIVO MODIFICATION OF THE SYNTHESIS ACTIVITY OF A METABOLITE BY MEANS OF THE MODIFICATION OF A GENE THE ACTIVITY OF WHICH IS NOT THE ORIGINAL ACTIVITY

The present invention relates to a method for the in vitro and in vivo artificial evolution of proteins, said method making it possible to modify the activity of a protein X so as to obtain a mutant capable of acting on an analogue of the natural substrate. A mutant of N-deoxyribosyltransferase (DTP) was obtained, said mutation conferring acquisition of the N-dideoxyribosyltransferase activity.

Generally, the obtaining of enzymes having activities modified with respect to their natural activity is an important consideration since this would make it possible to have access to powerful tools in numerous industrial applications, in particular in biotechnology.

Various solutions for carrying out directed mutations in a DNA molecule have been described in the state of the art. These techniques consist of introducing in vitro a mutation, deletion or insertion into a determined site in a DNA molecule for example using PCR. These various techniques are described in Hall, et al. Protein Eng. 4: 601 (1991); Hemsley, et al. Nucleic Acids Research 17: 6545-6551 (1989); Ho, et al. Gene 77: 51-59 (1989); Hultman, et al. Nucleic Acids Research 18: 5107-5112 (1990); Jones, et al. Nature 344: 793-794 (1990); Jones, et al. Biotechniques 12: 528-533 (1992); Landt, et al. Gene 96: 125-128 (1990); Nassal, et al. Nucleic Acids Research 18: 3077-3078 (1990); Nelson, et al. Analytical Biochemistry 180: 147-151 (1989); Vallette, et al. Nucleic Acids Research 17: 723-733 (1989); Watkins, et al. Biotechniques 15: 700-704 (1993); Weiner, et al. Gene 126: 35-41 (1993). Yao, et al. PCR Methods and Applications 1: 205-207 (1992) and in Weiner and al, Gene 151: 1/9-123 (1994).

However, it is impossible to know in advance what is the effect of a given mutation on the activity of a protein with such techniques.

Other methods consist of introducing mutations into the genome at random by using mutagenic agents (2-aminopurine, hydroxylamine or ACRIDINE) and selecting the cells or organisms showing the sought phenotype. Nevertheless, these methods lead to the introduction of numerous mutations, sometimes lethal, and are not suitable for causing a given protein to evolve for a precise purpose.

In order to respond to the needs and problems mentioned previously, the present invention proposes a method for modifying the activity of a protein combining in vitro and in vivo stages.

Within the framework of the invention it has been found that the introduction of mutations into the protein, followed by a confrontation with an analogue of the natural substrate within selective screening makes it possible to obtain a mutated protein having a strong activity on the new substrate. By repeating these operations, it is possible to obtain enzymes having an activity on substrates further and further removed from the initial natural substrate.

This method is particularly suitable for enzymes of the N-deoxyribosyltransferase (DTP) type.

Dideoxynucleosides such DDI and DDC and their derivatives are the most effective inhibitors known to date used in therapy against the HIV virus. These compounds are synthesized chemically, but can also be synthesized enzymatically. The N-deoxyribosyltransferase of *Lactobacillus leichmannii* (as well as that of *L. helveticus*), an enzyme which catalyzes the transfer of deoxyribose between two puric or pyrimidic bases is also capable of transferring 2',3'-dideoxyribose between these same bases (Carson and Wasson, 1988). Thus, several pyrazol (3,4-d) pyrimidine and triazolo (4,5-d) pyrimidine derivatives of 2',3'-dideoxycytidine and of the corresponding base have been synthesized (Fischer et al., 1990). The transfer reaction of 2',3'-dideoxyribose is however clearly less effective than that carried out with 2'-deoxyribose. For the purpose of having available an enzyme having a greater specific activity than the native enzyme for the transfer of 2',3-dideoxyribose, we combined a stage of random mutagenesis of the ntd gene of *L. leichmannii* with a stage of selection of the mutants using genetic screening.

A functional screen making it possible to select the production of uracil has been established in *E. coli*, by deleting the pyrC gene which controls the conversion of carbamyl aspartate to dihydroorotate as well as the codA and cdd genes which respectively control the deamination of cytosine and (deoxy)cytidine in order to produce the strain PAK 9. The strain PAK 9 has a uracil (u) requirement which cannot be satisfied by supplying uridine (R-U), deoxyuracil (dR-U) or dideoxyuracil (ddR-U). The use of dideoxyuracil (ddR-U) can however be selected in the strain PAK9 if a variant of N-deoxyribosyltransferase is capable of carrying out one of the following two reactions:

A random mutagenesis of the ntd gene of *L. leichmannii* was carried out, the mutated products were then cloned in a plasmid and the mixture used for transforming the strain PAK9. The transforming clones were selected in glucose mineral medium to which dideoxyuracil (ddR-U) and cytosine (C) were added. Several transformants were obtained and are capable of carrying out the exchange

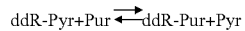

as well as

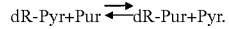

The nucleotide sequences of the different variants of NTD are identical and differ from the wild-type gene only by one mutation. Their enzyme activities were evaluated from crude extracts or purified proteins. The specific activity of NTD* is 10 times less than that of NTD for the transfer of deoxyribose but is 7 times greater for the transfer of dideoxyribose.

The selected enzyme is used in the enzymatic synthesis of 2',3'-dideoxynucleotides with natural or modified bases (5-halogeno-pyrimidines), comprising or not comprising radioelements. The method can be extended to the selection of variants capable of transferring derivatives of 2'-deoxyribose or 2',3'-dideoxyribose between bases (such as 3'-amino-2',3'-dideoxyribose or 3'-azido-2,3'-dideoxyribose).

Moreover, in the method according to the invention, cells in which a metabolic pathway has been inactivated can be used. The selective target consists of complementing this deficiency by producing the product P for which the cells are auxotrophic from an analogue of the natural substrate of protein X.

Alternatively, a protein X can be evolved by complementation of a related protein Y, X and Y both belonging to the same class of the EC enzyme nomenclature or to neighbouring classes.

DESCRIPTION

Thus, generally, the present invention relates to a method for the artificial evolution in vitro and in vivo of proteins, said method making it possible to evolve a protein X in vivo by complementation either of a related protein, or by complementation of an inactivated metabolic pathway.

Such a method makes it possible to evolve a protein X so as to modify its characteristics and comprises the following stages:
a) obtaining mutants X* from the sequence coding for the protein X by random mutagenesis;
b) transformation of cells comprising a phenotype [P-] with vectors comprising the mutated nucleic acids obtained in stage a) coding for the proteins X*, P-signifying that said cells are auxotrophic for the substance P, P being the product of the action of X on its natural substrate S;
c) culture of said cells in a medium comprising a substrate S*, S* being an analogue of the natural substrate S of protein X;
d) selection of the cells [P-:: X*] which have survived stage c) in which the proteins X* are capable of carrying out the biosynthesis of the product P from the substrate S.

The mutant protein X* obtained is a protein having an activity close to the natural protein X, X* and X belonging to common or neighbouring enzyme classes having at least the first three figures of the 4-figure EC international nomenclature classes. In order to pass from one class to another, the above-mentioned method can be repeated with, at each passage, the addition of an additional modification to the substrate analogue designated by S*. By "substrate analogue" is meant the natural substrate S of natural protein X, comprising a modification or an alteration. By "modification" of this substrate is meant the addition or suppression of at least one atom, group or substituent, the modification of the spatial conformation of the substrate (isomer, enantiomer, diastereoisomer). This modification can be minimal or significant from the structural point of view. In this case, where it is sought to substantially modify the activity of the protein (or enzyme), it is possible to repeat the method by further modifying the substrate S* at each new selection cycle. Little by little, the protein accumulates mutations which are responsible for the modification of its activity.

In this method, the cells used in stage b) are obtained by inactivation of at least one gene involved in the natural metabolic pathway leading to product P.

Thus, the obtained protein X* complements the deficiency of the natural metabolic pathway leading to product P in a medium provided with substrate S*.

By "complement" is meant the suppression of the auxotrophic phenotype resulting from the inactivation of the gene or the metabolic pathway.

Alternatively, the cells can be cells in which the gene coding for a protein related to X has been inactivated beforehand.

By "inactivation", is meant a deletion in whole or in part, an insertion, or a mutation rendering the gene inoperative. The inactivation can also consist of a modification leading to a Ts-type (temperature-sensitive) phenotype. In this case, the cells are cultured at temperatures which are not permissible for the selection phase (stages c) and d)).

Preferably, the related protein has at least the first three figures of the 4-figure EC international nomenclature.

Advantageously, the activity of protein X on substrate S is at least 2, 5, 10, 25, 50, 100 or 1000 times greater than its activity on substrate S*. In parallel, the activity of protein X* on substrate S* is at least 5, 10, 25, 50, 100 or 1000 times greater than its activity on substrate S.

Among the proteins referred to, there can be mentioned:

| EC Number | Name according to the international nomenclature |
|---|---|
| | the ribosyltransferases, such as for example: |
| 2.4.2.5 | Nucleoside ribosyltransferase. |
| 2.4.2.6 | Nucleoside deoxyribosyltransferase. |
| 2.4.2.7 | Adenine phosphoribosyltransferase |
| 2.4.2.8 | Hypoxanthine phosphoribosyltransferase. |
| 2.4.2.9 | Uracil phosphoribosyltransferase. |
| 2.4.2.10 | Orotate phosphoribosyltransferase. |
| 2.4.2.11 | Nicotinate phosphoribosyltransferase. |
| 2.4.2.12 | Nicotinamide phosphoribosyltransferase. |
| 2.4.2.14 | Amidophosphoribosyltransferase. |
| 2.4.2.17 | ATP phosphoribosyltransferase. |
| 2.4.2.18 | Anthranilate phosphoribosyltransferase. |
| 2.4.2.20 | Dioxotetrahydropyrimidine phosphoribosyltransferase. |
| 2.4.2.21 | Nicotinate-nucleotide-dimethylbenzimidazole phosphoribosyltransferase. |
| 2.4.2.22 | Xanthine-guanine phosphoribosyltransferase. |
| 2.4.2.29 | Queuine tRNA-ribosyltransferase. |
| 2.4.2.30 | NAD(+) ADP-ribosyltransferase. |
| 2.4.2.31 | NAD(P)(+)--arginine ADP-ribosyltransferase. |
| 2.4.2.36 | NAD(+)--diphthamide ADP-ribosyltransferase. |
| 2.4.2.37 | NAD(+)--dinitrogen-reductase ADP-D-ribosyltransferase. |
| | the kinases, such as for example: |
| 2.7.1.20 | Adenosine kinase. |
| 2.7.1.21 | Thymidine kinase. |
| 2.7.1.38 | Phosphorylase kinase. |
| 2.7.1.49 | Hydroxymethylpyrimidine kinase. |
| 2.7.1.74 | Deoxycytidine kinase (DCK). |
| 2.7.4.6 | Nucleoside-diphosphate kinase. |
| 2.7.4.7 | Phosphomethylpyrimidine kinase. |
| 2.7.4.8 | Guanylate kinase. |
| 2.7.4.9 | Thymidylate kinase. |
| 2.7.4.10 | Nucleoside-triphosphate--adenylate kinase. |
| 2.7.4.11 | (Deoxy)adenylate kinase. |
| 2.7.4.12 | T2-induced deoxynucleotide kinase. |
| 2.7.4.13 | (Deoxy) nucleoside-phosphate kinase. |
| | the nucleotidyl transferases, such as for example |
| 2.7.7.6 | DNA-directed RNA polymerase. |
| 2.7.7.7 | DNA-directed DNA polymerase. |
| 2.7.7.8 | Polyribonucleotide nucleotidyltransferase. |
| 2.7.7.19 | Polynucleotide adenylyltransferase. |
| 2.7.7.25 | tRNA adenylyltransferase. |
| 2.7.7.48 | RNA-directed RNA polymerase. |
| 2.7.7.49 | RNA-directed DNA polymerase. |
| 2.7.7.50 | mRNA guanylyltransferase. |
| | the phosphorylases, such as for example |
| 2.4.2.1 | Purine-nucleoside phosphorylase. |
| 2.4.2.2 | Pyrimidine-nucleoside phosphorylase. |
| 2.4.2.3 | Uridine phosphorylase. |
| 2.4.2.4 | Thymidine phosphorylase. |
| 2.4.2.7 | Adenine phosphoribosyltransferase. |
| 2.4.2.8 | Hypoxanthine phosphoribosyltransferase. |
| 2.4.2.9 | Uracil phosphoribosyltransferase. |
| 2.4.2.15 | Guanosine phosphorylase. |
| 2.4.2.23 | Deoxyuridine phosphorylase. |
| 2.4.2.28 | 5'-methylthioadenosine phosphorylase. |

Preferably, protein X is selected from the ribosyltransferases belonging to the EC classes 2.4.2.—, in particular the N-deoxyribosyltransferases of EC class 2.4.2.6.

Of course, other enzymes, in particular the metabolism or catabolism enzymes, can be the subject of a modification using the method according to the invention. These enzymes and their respective EC number are indexed by the Committee of the International Union of Biochemistry and Molecular Biology (IUBMB) at the following address: http://expasy.proteome.org.au/enzyme/

The random mutagenesis of stage a) can be carried out either by variation of the manganese concentration during the PCR reaction, or by use of promutagenic nucleotide analogues or also by the use of primers comprising a random sequence. Different techniques are described in the documents U.S. Pat. No. 6,323,030 (Methods for generating polynucleotides having desired characteristics by iterative selection and recombination), U.S. Pat. No. 6,177,263 (Recombination of polynucleotide sequences using random or defined primers), WO 01/66798 (Random truncation and amplification of nucleic acid), and EP1205547 (DNA mutagenesis by random fragmentation and reassembly).

The cells used within the framework of the invention are procaryotic or eucaryotic cells, preferably *E. coli*.

In a particular embodiment, the invention relates to a method as described above for evolving an N-deoxyribosyltransferase (DTP) so as to obtain an N-dideoxyribosyltransferase characterized in that it comprises the following stages:
a) obtaining DTP* mutants with the sequence coding for an N-deoxyribosyltransferase (DTP) by random mutagenesis;
b) transformation of cells comprising an [N-] phenotype with vectors comprising the mutated nucleic acids obtained in stage a) coding for the DTP* proteins, N-signifying that said cells are auxotrophic for at least one nucleoside, said nucleoside being the product of the action of DTP on its natural substrate dR-N;
c) culture of said cells in a medium comprising a substrate ddR-N;
d) selection of the [N-:: DTP*] cells which have survived stage c) in which the DTP* proteins are capable of carrying out the transfer of the dideoxyribose (ddR) from a dideoxyribonucleoside to another nucleoside leading to the production of the N nucleoside necessary for the survival of the cells.

By N nucleoside is meant a natural nucleoside, i.e. molecules constituted by a sugar bonded to a heterocyclic base by an N-glycosidic bond, the bases being pyrimidines (thymine, uracil, cytosine) or purines (adenine, guanine among the usual bases). By N-, is meant an [A-, T-, G-, C-, U- or I-] phenotype.

The NTD* enzyme obtained can be capable of recognizing and transferring a deoxyribose analogue such as dideoxyribose, but also acting on nucleoside analogues. Thus, the substrate analogue S* used can be a deoxyribonucleoside analogue comprising at least one chemical modification on the base and/or on the ribose.

More particularly, N-deoxyribosyltransferase (DTP) is the DTP of *Lactobacillus leichmannii* of SEQ ID No 1.

In this method, in stage b) ΔpyrC, Δcod A, Δcdd *E. coli* bacteria deficient in the metabolic pathway leading to uracil can be used. This bacterium is designated as being the PAK 9 strain deposited at the CNCM on 27 Jun. 2002 under No. 1-2902.

In a second feature, the invention relates to the mutated protein X* capable of being obtained from the method described above, characterized in that it has a modified activity relative to the initial protein X.

The protein X* can be a mutated N-deoxyribosyltransferase capable of being obtained from the method according to the invention having an N-dideoxyribosyltransferase activity.

A subject of the present invention is also a mutated N-deoxyribosyltransferase capable of being obtained from the methods described above, characterized in that it has an N-dideoxyribosyltransferase activity and/or an activity on deoxy or dideoxyribonucleoside analogues comprising a modified base.

Advantageously, the invention relates to the abovementioned mutated N-deoxyribosyltransferase characterized in that it comprises the sequence SEQ ID No 2 comprising the mutation G9S and in that it has an N-dideoxyribosyltransferase activity.

The invention also relates to a nucleic acid comprising a sequence coding for the mutated N-deoxyribosyltransferase (NTD*) mentioned above, in particular the sequence SEQ ID No 3.

The invention also relates to an expression vector comprising said coding sequence. This sequence can be fused to an effective promoter in eucaryotic and/or procaryotic cells. The vector can be a plasmid capable of transforming and remaining in *E. coli* The vector can remain in the bacterium in a stable or transitory manner.

The invention also relates to a host cell comprising a vector as described previously.

In a third feature, the invention relates to the use of an N-dideoxyribosyltransferase described above for the transfer of a dideoxyribose (ddR) from a dideoxyribonucleoside to another nucleoside. This enzyme obtained from the method according to the invention is particularly useful for the preparation of nucleoside analogues having anti-tumorous properties, in particular ddI or ddC.

Thus, the invention also relates to a method for the preparation of compounds comprising a stage consisting of utilizing a mutated protein defined above.

This method is particularly advantageous for the preparation of nucleoside or nucleotide analogues useful for the treatment of cancer or infectious diseases, in particular dideoxyribonucleosides, in particular ddC or ddI.

The invention also relates to the PAK 9 strain of *E. coli* of genotype ΔpyrC:: Gm, ΔcodA::Km, cdd::Tn10 deposited at the CNCM under accession number 1-2902.

Reference will be made to the legends of the figures hereafter in the remainder of the description.

LEGENDS

FIG. 1: Biosynthesis routes
FIG. 1a) the "de novo" synthesis of DNA from simple precursors.
FIG. 1b) the backup or recycling route which is much less costly in terms of energy and involving reactions of sugar transfer from preformed bases (originating from the hydrolytic degradation of amino acids and nucleotides).
FIG. 2: Catalytic cycle of NTD
FIG. 3: Reaction ddU+I=ddI+U for psu-ntdA
FIG. 4: Reaction ddU+I=ddI+U for psu-ntd*C
FIG. 5: Reaction dU+I=dI+U for pSU-ntdA
FIG. 6: Reaction of dU+I=dI+U for pSU-ntd*C

EXAMPLE 1

Enzymatic Synthesis of Nucleosides

The synthesis of nucleosides in *E. coli* can be carried out according to two methods; [Agnete MUNCH-PETERSEN (1983). "Metabolism of nucleotides, nucleosides and nucleobases in microorganisms" published by Academic Press] (see FIGS. 1a and 1b).

Two classes of enzymes exist which catalyze the transfer of a 2-deoxyribosyl towards a nitrogenous base; see hereafter and [Jane R. HANRAHAN & David W. HUTCHINSON (1992). "The enzymatic synthesis of antiviral agents". Journal of Biotechnology; vol. 23; 193-210. The latter are sometimes used for the synthesis of nucleoside analogues].

1.1 The Nucleoside Phosphorylases

See the article by [Thomas A. KRENITSKY, George W. KOASALKA & Joel TUTTLE (1981). "Purine nucleoside synthesis, an efficient method employing nucleoside phosphorylase". Biochemistry; vol. 20; 3165-3621].

The majority of the microorganisms (such as *E. coli*) use this synthesis route which commences with the "reversible" phosphorylation of a ribonucleoside to ribose-1-phosphate (or 2-deoxyribonucleoside to 2-deoxyribose-1-phosphate) from inorganic phosphate with release of the donor base (1) followed by the addition of the acceptor base (2).

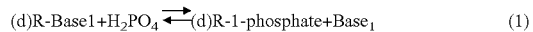

(d)R=(2-deoxy)ribose

[E]=PNPase (purine phosphorylase) or Deo D for Base=purine

Urd Pase (uridine phosphorylase) or UDP for Base=U (and T in marginal fashion)

dThd Pase (thymidine phosphorylase) or Deo A for Base=T (and U in marginal fashion)

These enzymes catalyze the same reaction with different substrates.

However, two classes of enzymes are distinguished [A. R. MUSHEGIAN & E. V. KOONIN (1994). "Unexpected sequence similarity between nucleosidases and phosphoribosyltransferases of different specificity". Protein Science; vol. 3; 1081-1088]:

on the one hand family I to which Deo D and UDP are attached (in *E. coli* the amino acid sequences which constitute them are very similar);

on the other hand family II comprising thymidine phosphorylases. Enzymes having the same function and being able to fix the same substrate (such as UDP and Deo A) do not therefore necessarily have related amino acid sequences.

1.2 The N-Deoxyribosltransferases (NTD)

The N-deoxyribosyltransferases catalyze the cleavage of the glycosidic bonds of the 2-deoxynucleotides. They are present in certain microorganisms which have little or no purine and pyrimidine phosphorylase (lactobacilla for example) [6-8]. They participate in the recycling of nucleotides.

Catalyzed Reactions According to the Type of Enzymes

Two types of enzyme have been characterized, [José HOLGUIN & Robert CARDDINAUD (1975). "Trans-N-Deoxyribosylase: substrate specific studies". European Journal of Biochemistry; vol. 54; 515-520].

Purine Deoxyribosyltransferase or NTD I:

This exclusively catalyzes the reversible transfer of a sugar with a puric base (donor base) to another purine (acceptor base).

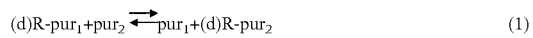

Pyrimidine/Purine deoxyribosyltransferase or NTD II:

This mostly catalyzes the transfer between purine and pyrimidine according to the following reversible equations:

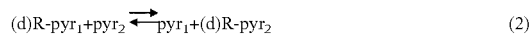

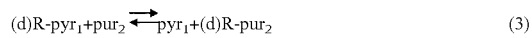

Reaction Mechanism (FIG. 2)

NTD II of *Lactobacillus delbruckii* would react according to a "ping-pong-bi-bi" mechanism which would involve two substrates and two products [José HOLGUIN & Robert CARDINAUD (1975). "Trans-N-Deoxyribosylase: Purification by affinity chromatography and characterization". European Journal of Biochemistry; vol. 54; 505-514; C. DANZIN & Robert CARDINAUD (1974). "Deoxyribosyl transfer catalysis with trans-N-deoxyribosylase. Kinetic studies of purine to purine trans-N-deoxyribosylase. European Journal of Biochemistry; vol. 48; 255-252; C. DANZIN & Robert CARDINAUD (1976). "Deoxyribosyl transfer catalysis with trans-N-deoxyribosylase. Kinetic studies of purine (pyrimidine) to purine (pyrimidine) trans-N-deoxyribosylase. European Journal of Biochemistry; vol. 62; 356-372].

It is assumed that the sugar of the donor nucleoside ($dBase_1$) binds to the enzyme in a covalent manner. An intramolecular reaction within this binary complex allows the cleavage of the β-glycosidic bond and the formation of a ternary complex E-deoxyribosyl-$Base_1$ followed by the release of the first product ($Base_1$). The acceptor base ($Base_2$) then binds to the binary intermediate and after intramolecular reaction on the active site of the enzyme, the second product ($dBase_2$) is released. The enzyme can then lead to another catalysis.

Physico-Chemical Properties

The two enzymes have a similar molecular weight (evaluated at approximately 100 kDa) but they differ in their heat stability (activity observed up to 45° C. for NTD I and 55° C. for NTD II) and their optimum pH (6.4 for NTD I and 6.0 for NTD II).

The ntd gene of *Lactobacillus delbruckii* coding for NTD II with a length of 471 bp codes for the synthesis of a protein with 157 amino acids and a total molecular weight of 110 kDa [William J. COOK, Steven A. SHORT & Steven E. EALICK (1990). "Crystallization & preliminary X-ray investigation of recombinant *Lactobacillus leichmanii* nucleoside 2-deoxyribosyltransferase". The Journal of Biological Chemistry; vol. 265; No. 5; 2682-2683]. The crystalline structure of the NTD II enzyme of *L. delbruckii* was determined with a resolution of 2.5 Å. This is a hexamer (trimer of dimers) constituted by six identical sub-units of 18 kDa. Each sub-unit has at its centre a parallel β sheet comprising five strands of various lengths and surrounded by four α helices arranged asymmetrically. Each one comprises an active site, but the six catalytic centres, in pairs separated by approximately 20 Å, require the participation of the side chains of the neighbouring sub-units [Shelly R. ARMSTRONG, William J. COOK, Steven A. SHORT & Steven E. EALICK (1996). "Crystal structures of nucleoside 2-deoxyribosyltransferase in native & ligand-bound forms reveal architecture of the active site". Structure; vol. 4; No. 1; 97-107]. The latter are involved in the positioning of the catalytic amino acid (glutamate 98) [David J. T. PORTER, Barbara M. MERRIL & Steven A. SHORT (1995). "Identification of the active site nucleophilic nucleoside 2-deoxyribosyltransferase as glutamic acid 98". The Journal of Biological chemistry; vol. 270; No. 26; 15551-15556].

Enzymatic Synthesis of Nucleoside Analogues

The transfer reactions, which are highly stereospecific, in the presence of an NTD I or NTD II transferase, exclusively produce the β anomer of the nucleoside (which avoids the stage of separation of the α and β isomers).

The enzyme has a great specificity vis-à-vis 2'-deoxyribonucleotides but tolerates a large number of modified analogues on the sugar or on the base. Thymidine and cytosine seem to be the most effective sugar donors. On the other hand the transfer can be carried out on a large panel of acceptor bases. The purines substituted in position 6 should for example be mentioned [D. BETBEDER, D. W. HUTCHINSON & A. O. RICHARDS (1989). "The stereoselective enzymatic synthesis of 9-β-D-2',3'dideoxynucleosides of N(6)-substituted purines". Antiviral Chem. Chemother; vol. 17; 4217-4222] and dYTP.

dYTP:

The imidazole-4-carboxamide called Y has been proposed as simplified purine. This analogue has the formula:

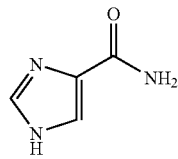

It has been reported that the nucleotide dYTP could be substituted for dATP or dGTP during the copying of the DNA which introduces mutations. There can also be mentioned the compounds described in WO 01/96354 (Institut Pasteur) of general formula:

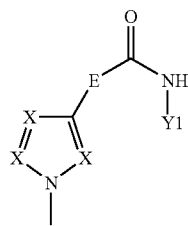

The NTD enzymes are shown to be capable of marginally catalyzing the exchange reaction between a 2',3'-dideoxyribose and an acceptor base:

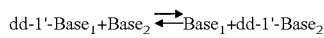

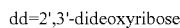

Nevertheless the speed of this transfer remains very low compared with that characterizing the exchange of deoxyriboses.

The 2',3'-dideoxyribonucleotides are evidently useful as chain terminators in the sequencing procedures. Moreover, 2',3'-dideoxyadenosine (ddA) and 2',3'-dideoxyinosine (ddI) are used for therapeutic purposes in particular in the case of the AIDS virus: these analogues effectively inhibit the replication of HIV (human immunodeficiency virus) [H. MITSUYA & S. BRODER (1987). "Strategies for antiviral therapy in AIDS". Nature; vol. 325; 773-778].

To this end, the invention provides a novel method for obtaining mutants of the NTD II enzyme in order to select mutant enzymes which have a stronger specificity vis-à-vis the 2',3'-dideoxyribonucleosides than the native enzyme.

EXAMPLE 2

Use of the Method According to the Invention for Obtaining NTD*

Materials and Methods

E. coli strains are cultured in Luria-Bertani (LB) medium or in MS minimum medium (Richaud et al. 1993). The antibiotics kanamycin, Km, chloramphenicol Cm, are used at a final concentration of 25 µg/ml; tetracycline, Tc and gentamycin, Gm, 10 µg/ml. The nucleosides and bases are used in the culture media at a final concentration of 0.3 mM. The molecular biology techniques were carried out according to Sambrook et al. (1989).

The amplification products are purified using QIAquick PCR purification (QIAgen).

The DNA fragments purified on agarose gel are extracted using the Jetsorb Kit (Genomed) or the QIAquick gel extraction kit (QIAgen). The plasmid DNA is purified using the QIAprep Spin Miniprep kit (QIAgen)

1—Construction of the Strain PAK9 (MG1655ΔpyrC:: Gm, ΔcodA::Km, cdd:: Tn10

*ΔcodA::Km:

```
The oligonucleotides codBL
                                    (SEQ ID No 4)
(5'-NNNCCCGGGCTTCTTGCTCGCTTCTCGTTTGG-3')
and cynTR
                                    (SEQ ID No 5)
(5'-NNGGATCCGTTTGACCGTAGCGGGCGAAC-3')
``` were used in order to amplify, starting from the DNA of the E. coli strain MG1655, a fragment of 3.3 kb containing the pyrC gene.

The PCR reactions are carried out in a final volume of 100 µL comprising 100 pmol of each oligonucleotide, 700 ng of DNA of the strain MG1655, the dNTPs at a final concentration of 200 µM, 10 µL of 10 times concentrated Taq polymerase reaction buffer (Roche) and 5 U of Taq polymerase (Roche). The amplification parameters are:

1 5-second cycle at 95° C., 25 cycles each comprising the following three stages: 30 seconds at 95° C., 30 seconds at 60° C., 2 minutes at 72° C., then a 10-minute cycle at 72° C. The amplification product was then digested by the restriction enzymes XmaI and BamHI, purified on gel and ligated to the pMTL22 plasmid (Chambers et al. 1988) digested by the same enzymes and purified on gel as above. The ligature mixture was used to transform the strain β 2033. The plasmid DNA of several transformants was prepared and used as DNA matrix in order to delete the codA gene using the oligonucleotides codBR (5'-NGAATTCTTATTCGACACTGTTAGC-CTCC-3') (SEQ ID No 6) and cynTL (5'-NGAATTCAC-GACTGGGTTACAGCGAGC-3') (SEQ ID No 7) under the same conditions and with the same parameters as above. The amplification product was then digested by the restriction enzyme EcoRI, purified on agarose gel and ligated to the EcoRI fragment of 1.2 kb of pUC4K (Pharmacia) conferring resistance to kanamycin. The ligature mixture was used in order to transform the strain β 2033. The plasmid DNA of several transformants resistant to kanamycin was prepared then used as DNA matrix for an amplification reaction with the oligonucleotides codBL and cynTR. The amplification product was then purified on agarose gel, digested by the restriction enzyme DpnI for 12 hours at 37° C. then extracted with phenol and precipitated from ethanol. The DNA taken up in solution in water was used in order to transform the strain MG1655 hosting the pKOBEG plasmid by electroporation (donated by J-M Ghigo, Unité des membranes bacteriennes). The transformant clones obtained on LB medium in the presence of kanamycin were then tested for sensitivity to 5-fluorouracil and resistance to 5-fluorocytosine. The deletion of the gene codA was also verified by amplification with the oligonucleotides codBL and cynTR.

*ΔpyrC::Gm:

```
The oligonucleotides
yeEL
                                       (SEQ ID No 8)
(5'-NNNCCCGGGGCCGACCTGCTGGCCCACTCTGACGG-3')
and dinR
                                       (SEQ ID No 9)
(5'-NNGGATCCCCCGGCGGCAGCGCCTACGGAACCGCTGCC-3')
``` were used in order to amplify, starting from the DNA of the *E. coli* strain MG1655, a fragment of 3.1 kb containing the pyrC gene according to the protocol described for codA The amplification product was then inserted into the pCR2.1-TOPO plasmid (Invitrogen, USA) and the mixture used to transform the strain TOP10F' (Invitrogen, USA). The plasmid DNA of the transformant clones was then prepared and used as matrix in an amplification reaction with the oligonucleotides

```
yceR
                                       (SEQ ID No 10)
(5'-NGAATTCTTAATCAGTAAATGGAATGACAATTTCGCC-3')
and dinL
                                       (SEQ ID No 11)
(5'-NGAATTCAAATCGTAGCTTCCTGTTGTCATTAGG-3').
```

The amplification parameters 1 5-second cycle at 95° C., 25 cycles each comprising the following three stages: 30 seconds at 95° C., 30 seconds at 65° C., 3 minutes at 72° C., then a 10-minute cycle at 72° C. The amplification product was then digested by the restriction enzyme EcoRI purified on gel and ligated to an EcoRI fragment of 1.1 kb conferring resistance to gentamycin. The ligature mixture was used to transform the strain β 2033. The plasmid DNA of the transformant clones resistant to gentamycin was then prepared and used in an amplification reaction with the oligonucleotides yceL and dinR. The amplification product was then purified on agarose gel then digested by the restriction enzyme DpnI for 12 hours at 37° C. and precipitated from ethanol after phenol extraction. The DNA was resolubilized in water then used to electroporate the strain MG1655 hosting the pKOBEG plasmid. The transformant clones were obtained on LB medium in the presence of gentamycin and uracil. The clones auxotrophic for uracil were also deleted from the pyrC gene.

*ΔpyrC::Gm, ΔcodA::Km, cdd::Tn10.

The codA::Km mutation carried by the strain PAK1 was transduced into the strain PAK2 (MG1655 ΔpyrC::Gm) using phage P1. The transductants were selected on LB medium supplemented with kanamycin, gentamycin and uracil. In the same manner the cdd::Tn10 was introduced into the strain PAK15 (MG1655 ΔpyrC::Gm, ΔcodA::Km) by transduction using a phage P1 stock prepared from the strain β7234 Δdeo, argE::am cdd::Tn10). The transductants were selected on the medium described above supplemented with tetracycline which made it possible to isolate the strain PAK9 (MG1655 ΔpyrC::Gm, ΔcodA::Km, cdd::Tn10). The strain PAK9 is auxotrophic for uracil (U), uridine (rU), and 2'-deoxycytidine (dC) and is incapable of growing on minimum mineral medium supplemented with glucose and cytosine (C), cytidine (rC) or 2'-deoxycytidine (dC).

2 Mutagenesis 2.1 Variation in the Manganese Concentration During the PCR Reaction The primers FP23 (5'-CGCCAGGGTTTCCCAGT-CACG) (SEQ ID No 12) and RP23 (5'-AGCGGATAA-CAATTTCACACAGG) (SEQ ID No 13) were used in order to amplify the cloned ntd gene in the pSU19 plasmid according to standard amplification conditions except for the final concentration of dNTPs: 20 μM and the $Mn^{2+}$ ion concentration which varies from 0 to 0.5 mM final according to the experiments. The amplification parameters 1 5-minute cycle at 95° C., 40 cycles each comprising the following three stages: 30 seconds at 95° C., 30 seconds at 53° C., 3 minutes at 72° C., then a 10-minute cycle at 72° C.

2.2 Mutagenesis by Incorporation of a dYTP Purine Analogue

Different amplification reactions were carried out using the oligonucleotides RP23 and FP23 as primers, the pSU19 plasmid containing the ntd gene as DNA matrix. In order to substitute the dATP, the following concentrations were used: dYTP (1 mM), dATP, dCTP and dTTP (200 μM) dGTP varying from 1 to 5 μM. In order to substitute the dGTP, the following concentrations were used: dYTP (1 mM), dATP, dCTP and dTTP (200 μM) dGTP varying from 1 to 5 μM. The amplification parameters are the same as those which are described above except for the third stage where the extension time is 10 minutes. A second amplification reaction is then carried out under the standard conditions using 10 μL of the first amplification.

3—Cloning and Selection

The purified amplification products are digested over 2 hours at 37° C. by the restriction enzymes BamHI and HindIII. After migration at 150 V over 45 minutes, they are purified by 1% agarose gel extraction using the QIAquick gel extraction kit (QIAgen).

The pSU19 plasmid is digested by the same enzymes and purified according to the same procedure.

The ligatures carried out in a volume of 20 μL include 15 ng of the amplification products, 50 ng of pSU19 digested by BamHI-HindIII, 2 μL of 10× concentrated T4 DNA ligase reaction buffer and 6 U of T4 DNA ligase. The reaction is carried out at 16° C. over 18 hours.

The ligature products are then dialyzed on Millipore filter (0.05 μm; 13 mm) for 30 minutes then used in order to transform the strain PAK9, prepared according to the protocol described by Dower et al. (1987), by electroporation.

1 to 5 μL of ligated DNA mixed with 50 μL of the strain PAK9 in a 2-mm cuvette are subjected to a 2.5 kV charge. After incubation for an hour at 37° C. in 1 ml of LB medium supplemented with uracil (0.3 mM), two successive washings with 1×1 ml MS medium are carried out.

450 μL of suspension are plated on glucose mineral agar medium supplemented with Cm, ddU and C. The dishes are incubated at 37° C. over 4 days. The selected colonies are then isolated on the same medium.

The plasmid DNA of the isolated colonies is prepared from culture in LB medium supplemented with Cm and U. Sequencing was carried out by MWG-BIOTECH.

4—Measurement of the Enzymatic Activity of the Crude Extracts of the Different Mutants 4.1 Preparation of the Crude Extracts The precultures are obtained after inoculation of an isolated colony in 5 mL of LB medium containing Cm and U for the strain PAK9 followed by incubation overnight under stirring at 37° C.

The next day, 15 mL of LB medium, Cm and U are inoculated at an $OD_{600}$=0.01. The cultures are then incubated at 37° C. until an OD comprised between 0.8 and 1 is reached.

The cells are then centrifuged at 4,000 rpm for 30 minutes at 4° C., the pellet is resuspended in 10 ml of 50 mM phosphate buffer ($Na_2HPO_4$+$NaH_2PO_4$) (pH=7.5). After centrifugation, the pellet is resuspended in 1 ml of the same buffer. The cells, preserved in ice, then undergo three 30-second cycles of sonication and 30-second cycles of rest. After centrifugation at 12,000 rpm for 2×15 minutes at 4° C.; the supernatants are recovered and stored at −20° C.

4.2 Enzymatic Reaction

50 μL of enzyme extract are added to 200 μL of 100 mM citrate buffer, pH 6.44 in the presence of ddU or dU at 3 mM final and of C at 1 mM final for the strain PAK9, the whole is incubated at 37° C. The progress of the reaction is monitored by TLC (Silica; eluent: MeOH—$CH_2Cl_2$ (20/80)). The products are developed under UV, and the sugars developed by Zücker reagent. The disappearance of the substrates and the formation of the products are also quantified by HPLC analysis. The different products are separated by analytical HPLC with a reversed-phase column (100-5C18) using a flow rate of 1 ml/min and a $CH_3CN$ 5-25% linear gradient in a 10 mM triethylammonium acetate buffer at pH 7.5 for 20 minutes.

5—Overproduction and Purification of the Native N-deoxyribosyltransferase and LL7 mutant.

```
The oligonucleotides
                                       (SEQ ID No 14)
5'-GATATACATATGCCAAAAAAGACGATCTAC
and
                                       (SEQ ID No 15)
5'-NNGGATCCTTAGTATACGGCACCTTCGTAGAAGTCG
``` were used as primer in an amplification reaction under standard conditions using the cloned ntd gene in pSU19 or mutant 7 previously selected as DNA matrix. Each amplification product was digested by the restriction enzymes NdeI and BamHI for 2 hours at 37° C., purified on agarose gel and inserted into the pET24a plasmid (NOVAGEN) digested by the same enzymes, then the ligature mixture used to transform the strain β 2033. The plasmid DNA of the colonies was prepared and digested by the enzymes NdeI and BamHI. Those the sequence of which was correct were used in order to transform the strain BL21 (DE3)/pLYS (NOVAGEN). The overproduction of the two enzymes was obtained from cultures of 500 ml of LB medium supplemented with Km and Cm. These cultures were induced at an $OD_{600}$=1 by the addition of IPTG (0.4 mM), the incubation being continued for 2 hours at 37° C.

The cells are then centrifuged for 15 minutes at 4000 rpm at 4° C., washed in 50 ml of phosphate buffer then the pellet obtained after centrifugation is stored overnight: at −20° C. The bacterial pellet resuspended in 20 ml of phosphate buffer is then lyzed by passing through a French press at 14000 psi. The lysate is centrifuged for 90 minutes at 50,000 rpm. The supernatant containing the soluble proteins is then precipitated with ammonium sulphate (55% saturation). The precipitate obtained after centrifugation at 13,900 rpm (20,000 g) for 30 minutes at 4° C. is resuspended in 5 ml of 100 mM phosphate buffer, pH 7.5, then dialyzed overnight at 4° C. against the same buffer at pH 6.0. The enzyme extract is then heated at 60° C. for 5 minutes then immediately replaced in ice. The denatured proteins are eliminated by centrifugation at 20,000 rpm for 30 minutes at 4° C. The purity of each enzyme is then analyzed by SDS-PAGE gel and the concentration determined by Bradford assay using a BSA range as standard. The measurement of the enzyme activities is carried out as described in paragraph 4.2.

Results

Activity Tests of Enzymatic Extracts

The activity present in the prepared enzymatic extract is assayed following the appearance of the product on TLC. Two types of reaction are tested depend on whether the transferred sugar is a deoxyribose or a dideoxyribose.

After incubation for 3 hours at 37° C., only the mutant extracts catalyze the transfer reaction

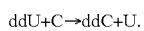

Like the wild-type strain, they are also capable of transferring deoxyribose but at an apparently slower speed.

On the other hand the reactions

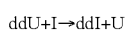

as well as

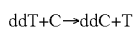

have also produced positive results with these four extracts. These results show that with a dideoxypyrimidine as donor, the acceptor base can be a purine or a pyrimidine.

Moreover, the extracts originating from the various mutants seem to behave in the same manner. We pursued the kinetic study more particularly on the mutant pSU-ntd*C by comparing its activity to that of the wild-type strain pSU-ntdA using HPLC analyses.

Kinetic Monitoring of the Reactions at pH=7.5

We chose to consider reactions (1) and (2) and to take dU or ddU as donor and hypoxanthine I as acceptor.

  (1)

  (2)

The donor nucleosides are introduced in excess relative to the acceptor base (in a ratio of 3:1) in order to shift the equilibrium of the reactions in the direction of the sugar transfer.

HPLC analysis allows precise monitoring of the progress of the reaction as a function of time. The reaction products are characterized by a retention time t (given for a gradient of 0 to 15 of acetonitrile in a buffer over 20 minutes). Detection is carried out at 254 nm.

|         | U   | I   | dU  | dI  | ddU  | ddI  |
|---------|-----|-----|-----|-----|------|------|
| t (min) | 3.8 | 6.7 | 7.8 | 9.3 | 10.4 | 11.9 |

Reaction (1): Transfer of Deoxyribose

Figure 3:
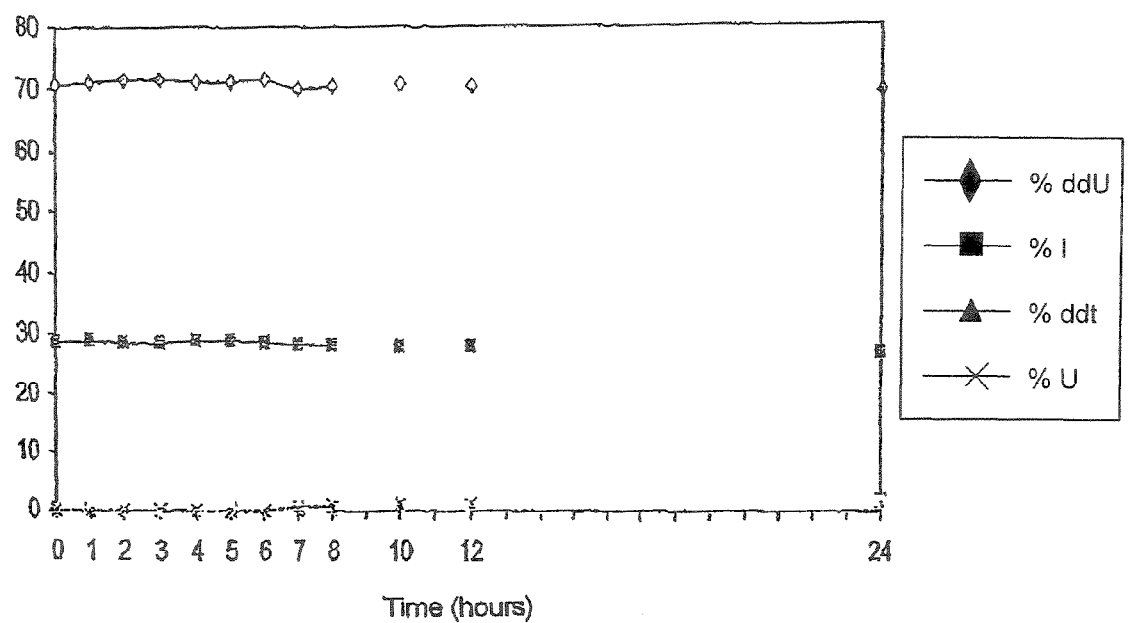

As shown in FIG. 3, the N-deoxyribosyltransferase NTD II of pSU-ntd A rapidly catalyzes this exchange: the formation of U and dI is virtually immediate. After one hour at 37° C., more than 70% of hypoxanthine I (limiting reagent) has reacted and the formation of dI is noted. After four hours; 88% of I introduced initially with a view to producing dI and U has been consumed.

Figure 4:
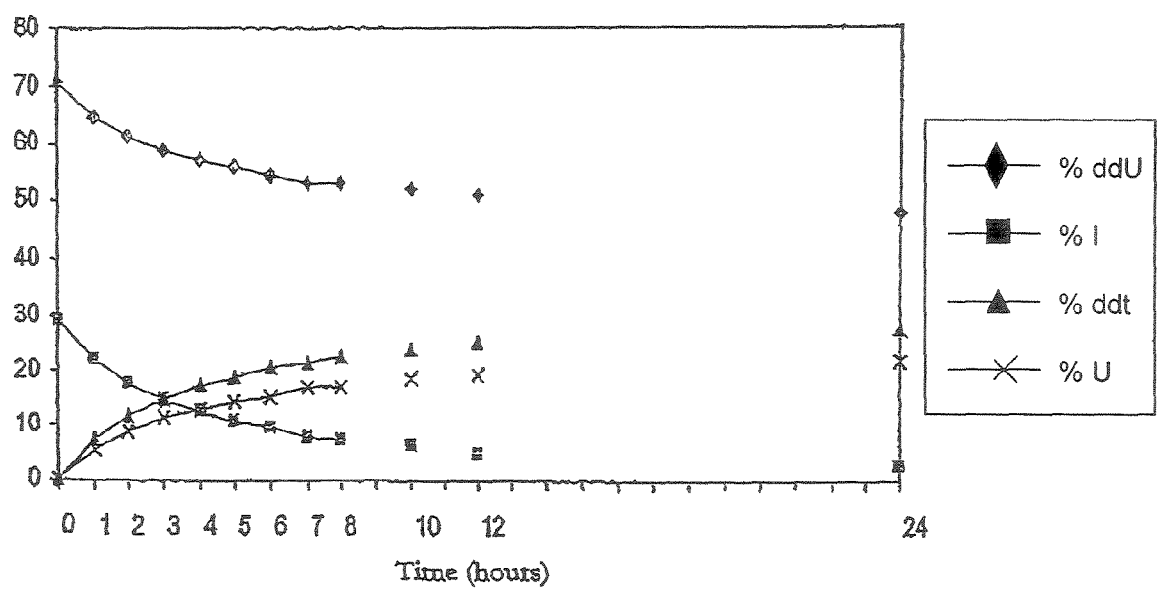

The mutant strain is also capable of carrying out the exchange of deoxyribose but with much slower kinetics than the wild-type strain. An hour at 37° C. is necessary before the appearance of the products: approximately 30% of I have then been transformed (FIG. 4). Even if the reaction proves to be slower, equilibrium is reached after twelve hours in both cases.

Reaction (2): Transfer of Dideoxyribose

Figure 5:
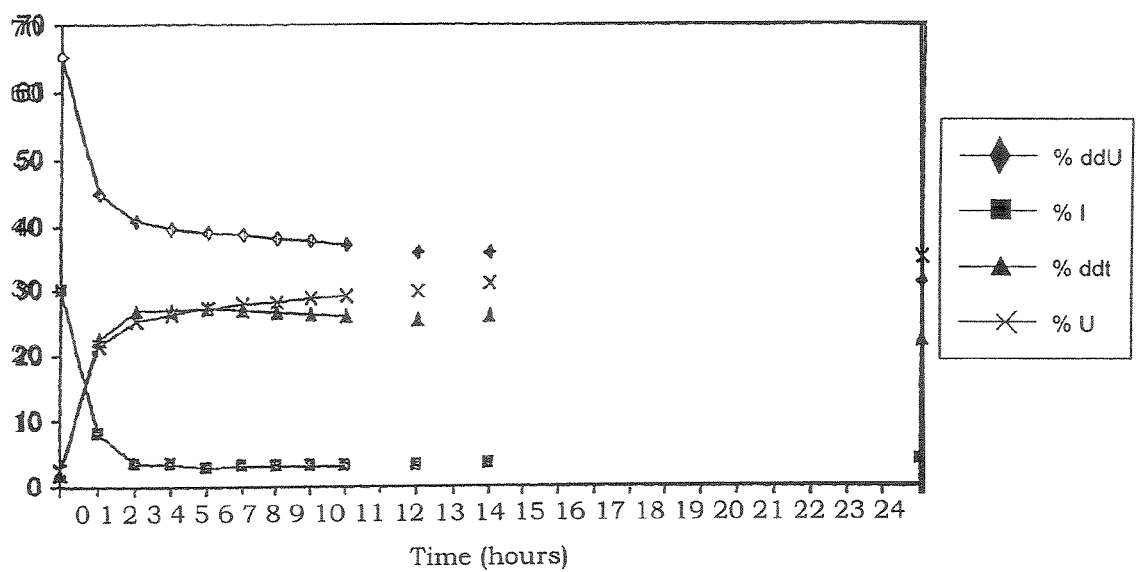

No conversion of ddU to ddt is obtained with the extracts expressing the wild-type ntd gene, even after 24 hours at 37° C. (FIG. 5).

Figure 6:
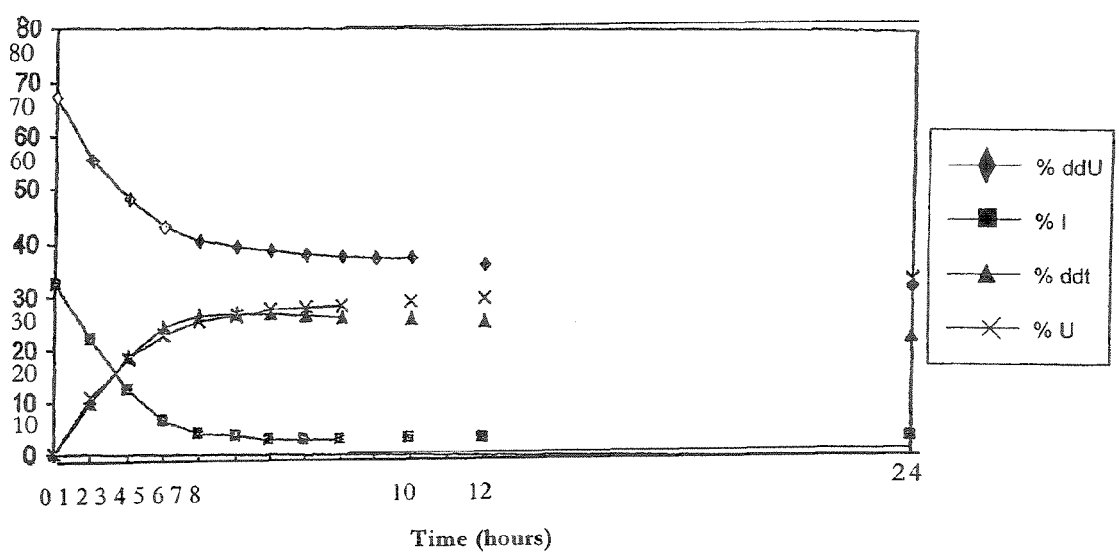

On the other hand, with the extracts expressing the mutated gene, after one hour N-deoxyribosyltransferase catalyzes the formation of ddI and U with 25% of hypoxanthine having reacted (FIG. 6). FIG. 6 shows the relative proportions of the reagents and of the products for the two strains after three hours at 37° C. In the case of the extract containing the mutant enzyme after the consumption of more than 50% of I over four hours the reaction diminishes. No shifting of the equilibrium reached is detected after 24 hours. The reaction is shown to be virtually total (more than 90% of I has reacted in order to synthesize ddI and U). On the other hand with the control strain only 5% of synthesizable ddI is produced.

The NTD* enzyme produced by the pSU-ntd*C plasmid proves to be an excellent catalyst of the exchange reaction vis-à-vis 2',3'-dideoxyribose. Two major features have been modified: the speed has clearly increased and the state of equilibrium is broadly shifted in favour of the transfer of 2',3'-dideoxyribose. Thus the reaction has become both rapid and quantitative.

CONCLUSION

Different random mutagenesis protocols were tested with a view to modifying the specificity of N-deoxyribosyltransferase vis-à-vis the dideoxyriboses. The first is based on alteration of the fidelity of the Taq polymerase in the presence of manganese, which under the tested conditions (0.25 mM) generates a limited number of mutations per clone. The second protocol is based on the use of a nucleoside analogue, dYTP, instead of dGTP which is described in order to generate a low level of mutations. It would therefore seem that the conversion of an N-deoxyribosyltransferase activity to an N-dideoxyribosyltransferase activity requires only one or two mutations.

The number of mutants retained after the stage of selection on a dish remains very low compared with the total number of mutants generated. This observation underlines the power of a selection based on nutritional requirements.

On the other hand the mutated N-deoxyribosyltransferases NTD* expressed in the strain ΔpyrC ΔcodA Δcdd can catalyze various exchange reactions such as:

$ddU+C=ddC+U;$ $ddT+C=ddC+T$ and $ddU+I=ddI+U.$

A kinetic study of this last reaction shows that the speed of transfer of dideoxyribose by the mutated enzyme has been increased by at least a factor of 10 compared with that of the wild-type enzyme.

Moreover, the reaction catalyzed by the N-deoxyribosyltransferase NTD* can be considered as rapid and total with more than 90% of the limiting reagent consumed.

The mutated enzyme is also capable of catalyzing the exchange of deoxyribose but at a reaction speed reduced by half compared with that observed for the native enzyme. Moreover, it is possible to imagine the reiteration of an evolution directed to the mutated genes. Thus, an enzymatic synthesis of antiviral agents catalyzed by these mutated enzymes could be envisaged. This perspective would simplify the preparation of the dideoxynucleotides, obtained in general by reduction of the corresponding deoxynucleotides.

The method of random mutagenesis associated with a selection phase is applicable to numerous genes coding for example for the synthesis of biologically useful products. It opens up a prodigious variability of genes mutated from a single gene and can thus make it possible to improve an activity already existing in certain enzymes or even to generate a new activity.

REFERENCES

Chambers S P, Prior S E, Barstow D A, Minton N P. (1988) The pMTL nic-cloning vectors. Improved pUC polylinker regions to facilitate the use of sonicated DNA for nucleotide sequencing. Gene 68: 139-49

Munier H, Gilles A M, Glaser P, Krin E, Danchin A, Sarfati R, Barzu O. (1991) Isolation and characterization of catalytic and calmoduliN-binding domains of *Bordetella pertussis* adenylate cyclase. Eur J. Biochem. 196: 469-74.

Dower W J, Miller J F, Ragsdale C W. (1988) High efficiency transformation of *E. coli* by high voltage electroporation. Nucleic Acids Res. 16: 6127-45.

Bartolome B, Jubete Y, Marinez E, de la Cruz F. (1991) Construction and properties of a family of pACYC184-derived cloning vectors compatible with pBR322 and its derivatives. Gene. 102: 75-8

Carson D. A. & Wasson D. B. (1988) Synthesis of 2',3'-dideoxynucleosides by enzymatic trans-glycosylation. Biochem. Biophys. Res. Comm. 155: 829-834.

Fischer, X., Kaun, E. and Genz, U. (1990) 2',3'-Dideoxyribofuranosides and process for their production. Ger. Offen. DE 3840160.

Richaud C, Mengin-Lecreulx D, Pochet S, Johnson E J, Cohen G N, Marliere P. (1993) Directed evolution of biosynthetic pathways. Recruitment of cysteine thioethers for constructing the cell wall of *Escherichia coli*. J Biol. Chem. 268: 26827-35.

The invention claimed is:

1. A method for evolving a N-deoxyribosyltransferase (DTP) so as to modify its characteristics, the method comprising
   a) obtaining mutants X* from the sequence coding for the DTP by random mutagenesis;
   b) transforming *E. coli* cells comprising at least one genotype ΔpyrC, ΔcodA, and Δcdd and which *E. coli* cells are deficient in the metabolic pathway leading to uracil and a phenotype [P-] with vectors comprising the mutated nucleic acids obtained in stage a) coding for the mutants X*, P-signifying that said *E. coli* cells are auxotrophic for the substance P, P being the product of the action of X on its natural substrate S;
   c) culturing said *E. coli* cells in a medium comprising a substrate S*, S* being an analogue of the natural substrate S of DTP; and
   d) selecting the *E. coli* cells [P-:: X*] which have survived stage c) in which the mutants X* are capable of carrying out the biosynthesis of the product P from the substrate S.

2. The method according to claim 1, wherein the mutant X* is a protein having an activity similar to the natural DTP.

3. The method according to claim 1, wherein the *E. coli* cells used in stage b) are obtained by inactivation of at least one gene involved in the natural metabolic pathway leading to product P.

4. The method according to claim 3, wherein the mutant X* complements the deficiency of the natural metabolic pathway leading to product P in a medium provided with substrate S*.

5. The method according to claim 1, wherein the activity of the DTP on substrate S is at least 2 times greater than its activity on substrate S*.

6. The method according to claim 1, wherein the activity of mutant X* on substrate S* is at least 10 times greater than its activity on substrate S.

7. The method according to claim 1, wherein the random mutagenesis of stage a) is carried out either by variation of manganese concentration during a PCR reaction, with promutagenic nucleotide analogues, or also with primers comprising a random sequence.

8. A method for evolving an N-deoxyribosyltransferase (DTP) so as to obtain an N-dideoxyribosyltransferase, the method comprising:
   a) obtaining DTP* mutants with the sequence coding for an N-deoxyribosyltransferase (DTP) by random mutagenesis;
   b) transforming *E. coli* cells comprising at least one genotype ΔpyrC, ΔcodA, and Δcdd and which *E. coli* cells are deficient in the metabolic pathway leading to uracil and an [N-] phenotype with vectors comprising the mutated nucleic acids obtained in stage a) coding for the DTP* mutants proteins, N-signifying that said *E. coli* cells are auxotrophic for at least one nucleoside, said nucleoside being the product of the action of DTP on its natural substrate dR-N;
   c) culturing said *E. coli* cells in a medium comprising a substrate ddR-N; and
   d) selecting the [N-:: DTP*] *E. coli* cells which have survived stage c) in which the DTP* proteins mutants are capable of carrying out the transfer of the dideoxyribose (ddR) from a dideoxyribonucleoside to another nucleoside leading to the production of the N nucleoside necessary for the survival of the *E. coli* cells.

9. The method according to claim 8, wherein the N-deoxyribosyltransferase (DTP) is the DTP of *Lactobacillus leichmannii* of SEQ ID No 1.

10. The method according to claim 8, wherein the activity of DTP* mutants on substrate ddR-N is at least 5 times greater than its activity on dR-N.

11. The method according to claim 8, wherein the activity of DTP* mutants on substrate ddR-N is at least 10 times greater than its activity on dR-N.

* * * * *